United States Patent
No et al.

(10) Patent No.: US 8,572,993 B2
(45) Date of Patent: Nov. 5, 2013

(54) APPARATUS FOR DETECTING FOGGED WINDOW OF VEHICLE

(75) Inventors: Hag-chul No, Seoul (KR); Kyung-sun Kim, Seoul (KR)

(73) Assignee: Auto Electronic Corporation (KR)

( * ) Notice: Subject to any disclaimer, the term of this patent is extended or adjusted under 35 U.S.C. 154(b) by 877 days.

(21) Appl. No.: 12/681,174

(22) PCT Filed: Oct. 1, 2007

(86) PCT No.: PCT/KR2007/004778
§ 371 (c)(1),
(2), (4) Date: Apr. 1, 2010

(87) PCT Pub. No.: WO2009/044942
PCT Pub. Date: Apr. 9, 2009

(65) Prior Publication Data
US 2010/0206047 A1    Aug. 19, 2010

(51) Int. Cl.
*G05D 22/02*    (2006.01)
(52) U.S. Cl.
USPC ............... 62/176.6; 236/44 C; 73/29.05
(58) Field of Classification Search
USPC ............ 62/176.1, 176.6, 177; 236/44 C; 73/29.05; 165/230, 231
See application file for complete search history.

(56) References Cited

U.S. PATENT DOCUMENTS

| | | | |
|---|---|---|---|
| 6,422,062 B1 | 7/2002 | King et al. | |
| 7,770,433 B2 * | 8/2010 | Rothacher et al. | 73/29.05 |
| 7,900,464 B2 * | 3/2011 | Aoki et al. | 62/176.6 |
| 2006/0203879 A1 | 9/2006 | Ruttiger et al. | |
| 2006/0207325 A1 | 9/2006 | Kataoka et al. | |

FOREIGN PATENT DOCUMENTS

| | | |
|---|---|---|
| JP | 61-056567 | 3/1986 |
| JP | 04-356257 | 12/1992 |
| JP | 2006-256496 | 9/2006 |
| JP | 2007-505302 | 3/2007 |
| KR | 10-2004-0005306 | 1/2004 |
| KR | 10-2006-0009664 | 2/2006 |
| KR | 10-2006-0118688 | 11/2006 |

OTHER PUBLICATIONS

International Search Report—PCT/KR2007/004778 dated Jun. 26, 2008.
Written Opinion—PCT/KR2007/0004778 dated Jun. 26, 2008.

* cited by examiner

*Primary Examiner* — Marc Norman
(74) *Attorney, Agent, or Firm* — Cantor Colburn LLP

(57) ABSTRACT

A fog sensing apparatus for vehicle windows is provided. The fog sensing apparatus includes: a temperature/humidity sensor module including a glass surface temperature sensor for measuring a temperature of a glass surface of the vehicle window, and a humidity sensor for measuring relative humidity around the glass surface of the vehicle window; a flexible printed circuit board on which the temperature/humidity sensor module is mounted, which a temperature measurement part of the glass surface temperature sensor contacts, and on which a conductive pattern is formed to be connected to electrode terminals of the glass surface temperature sensor and electrode terminals of the humidity sensor; a substrate assembly having a through hole for the temperature/humidity sensor module to pass through, and connection terminals connected to the conductive pattern; and a case covering the substrate assembly, the substrate assembly interposed between the case and the flexible printed circuit board.

8 Claims, 2 Drawing Sheets

APPARATUS FOR DETECTING FOGGED WINDOW OF VEHICLE

TECHNICAL FIELD

The present invention relates to a fog sensing apparatus for vehicle windows, and more particularly, to a fog sensing apparatus for vehicle windows which can effectively prevent fog from forming on a vehicle window by correctly measuring a temperature of the glass surface of the vehicle window.

BACKGROUND ART

In general, a vehicle is equipped with a sensor for preventing fog from forming on the vehicle's window. The sensor is connected to an air conditioning system of the vehicle to automatically remove fog formed on the vehicle's window, thereby supporting safe driving.

Various apparatuses for preventing fog from forming on a vehicle window have been developed both at home and abroad. An example of such apparatuses is disclosed in U.S. Pat. No. 6,422,062 entitled "an integrated glass fog sensor unit" by Delphi Corp. In the conventional technique, the integrated glass fog sensor unit includes a glass surface temperature sensor, an ambient air temperature sensor, and a relative humidity sensor, and measures humidity and a temperature at the same location by locating the relative humidity sensor adjacent to the ambient air temperature sensor to obtain an exact dew point temperature.

DISCLOSURE OF INVENTION

Technical Problem

However, in the conventional technique, since the temperature measuring part of the glass surface temperature sensor is attached to a glass surface via an adhesive layer to measure a temperature of the glass surface, a gap may be formed between the temperature measuring part and the adhesive layer when the adhesive layer is attached to a curved glass surface, when foreign materials are collected between the temperature measuring part and the adhesive layer, etc., which may make the glass surface temperature sensor to measure a wrong temperature value and thus may cause fog to form on the glass surface.

Technical Solution

The present invention provides a compact fog sensing apparatus which effectively prevents fog from forming on a glass surface by correctly measuring a temperature of the glass surface.

Advantageous Effects

As described above, the fog sensing apparatus according to the present invention can prevent fog from forming on a vehicle window in connection with an air conditioning system of a vehicle by correctly measuring a temperature of the glass surface of the vehicle window to obtain an exact dew point temperature.

BEST MODE FOR CARRYING OUT THE INVENTION

According to an aspect of the present invention, there is provided a fog sensing apparatus for a vehicle window, including: a temperature/humidity sensor module including a glass surface temperature sensor for measuring a temperature of a glass surface of the vehicle window, and a humidity sensor for measuring relative humidity around the glass surface of the vehicle window; a flexible printed circuit board on which the temperature/humidity sensor module is mounted, which a temperature measurement part of the glass surface temperature sensor contacts, and on which a conductive pattern is formed to be connected to electrode terminals of the glass surface temperature sensor and electrode terminals of the humidity sensor; a substrate assembly having a through hole for the temperature/humidity sensor module to pass through, and connection terminals connected to the conductive pattern; and a case covering the substrate assembly, the substrate assembly interposed between the case and the flexible printed circuit board.

MODE FOR THE INVENTION

Figure 1:
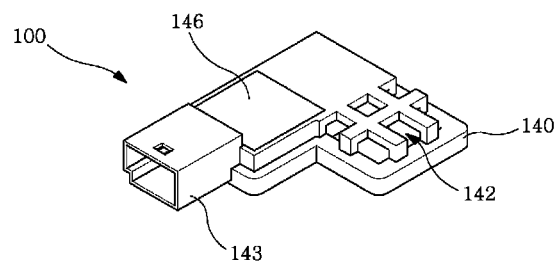
FIG. 1 is a perspective view of a fog sensing apparatus for vehicle windows according to an embodiment of the present invention.
Figure 2:
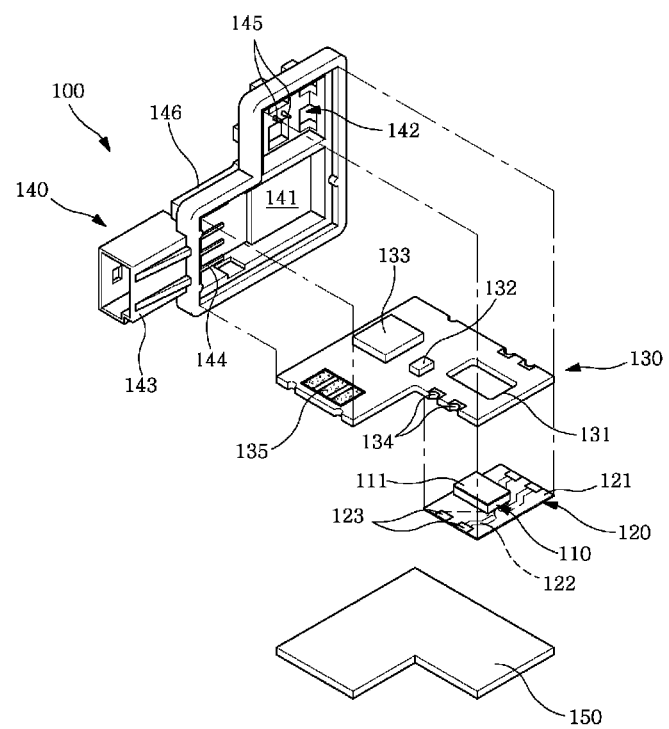
FIG. 2 is an exploded perspective view of the fog sensing apparatus illustrated in FIG. 1.

FIG. 1 is a perspective view of a fog sensing apparatus for vehicle windows according to an embodiment of the present invention, and FIG. 2 is an exploded perspective view of the fog sensing apparatus illustrated in FIG. 1.

Referring to FIGS. 1 and 2, the fog sensing apparatus 100 for vehicle windows includes a temperature/humidity sensor module 110, a flexible printed circuit board (FPCB) 120, a substrate assembly 130, and a case 140.

The temperature/humidity sensor module 110 includes a glass surface temperature sensor for measuring a temperature of the glass surface 10 (see FIG. 4) of a vehicle window, and a humidity sensor for measuring relative humidity around the glass surface 10. The glass surface temperature sensor may be a thermistor, or any other well-known temperature sensor. A temperature measurement part of the glass surface temperature sensor is exposed, and two electrode terminals are drawn out from the glass surface temperature sensor. Here, the temperature measurement part may be a part of the electrode terminals. Also, the humidity sensor may be a capacitive humidity sensor. If the humidity sensor is a capacitive humidity sensor, the humidity sensor includes two electrodes and a hygroscopic high molecular thin film therebetween. Likewise, electrode terminals are drawn out from the humidity sensor.

Meanwhile, the temperature/humidity sensor module 110 may be a Micro Electro Mechanical Systems (MEMS) type sensor using a MEMS technology so that it can be miniaturized. As the temperature/humidity sensor module 110 is miniaturized, a glass surface area which the temperature/humidity sensor module 110 contacts is less influenced by the curve of the glass surface. A filter 111 can be installed in an air inflow channel formed in the humidity sensor of the temperature/humidity sensor module 110. The filter 111 removes foreign materials from air supplied through an air inflow hole 142 of the case 140, and supplies only humidity to the humidity sensor. The filter 111 may be a membrane filter. The membrane filter may be made of a material such as Polytetrafluoroethylene (PTFE) Teflon or a nonwoven fabric.

The temperature/humidity sensor module 110 is mounted on the flexible printed circuit board 120. The flexible printed circuit board 120 contacts the temperature measurement part of the glass surface temperature sensor so that heat from the flexible printed circuit board 120 can be directly transferred to the temperature measurement part of the glass surface temperature sensor. That is, since heat is transferred through the flexible printed circuit board 120 with a relatively large area from the glass surface 10 to the temperature measurement part of the glass surface temperature sensor, and the flexible printed circuit board 120 can be attached to an adhesive layer 150 (which will be described later) while being curved along the curve of the glass surface 10, heat from the glass surface 10 can be transferred to the temperature measurement part of the glass surface temperature sensor without heat loss. Therefore, it is possible to correctly measure a temperature of the glass surface 10 and effectively prevent fog from forming on the glass surface 10.

Figure 3:
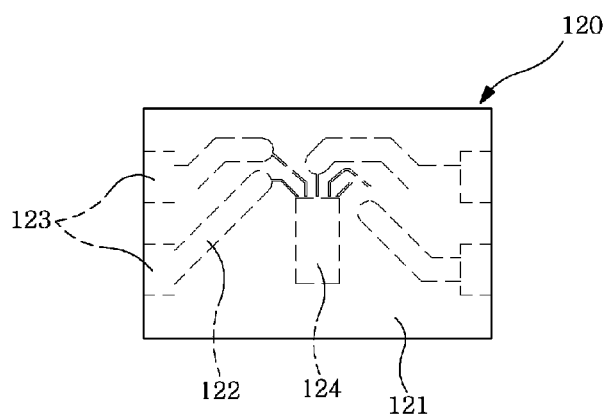
FIG. 3 is a wiring diagram of a flexible printed circuit board (FPCB) included in the fog sensing apparatus illustrated in FIG. 2.

In order to transfer heat from the flexible printed circuit board 120 to the temperature measurement part without heat loss, the flexible printed circuit board 120 can further include a conductive part 124 made of a conductive material in a portion where the flexible printed circuit board 120 contacts the temperature measurement part, as illustrated in FIG. 3. Since heat transfer of the glass surface 10 deteriorates and a temperature measurement error increases if the flexible printed circuit board 120 is too thick, it is preferable that the flexible printed circuit board 120 has a thickness less than 0.1 mm.

The flexible printed circuit substrate 120 includes a conductive pattern 122 for connecting the respective electrode terminals of the glass surface temperature sensor and humidity sensor to connection terminals 134 of the substrate assembly 130. Here, the conductive pattern 122 may be a copper foil pattern. As illustrated in FIG. 3, the conductive pattern 122 is formed on a base board 121, and includes lead terminals 123 which are formed on the edge portions of the base board 121 in a manner to be exposed in correspondence to the connection terminals 134 of the substrate assembly 130.

The substrate assembly 130 includes a through hole 131 through which the temperature/humidity sensor module 110 passes. The connection terminals 134 are connected to the conductive pattern 122 of the flexible printed circuit board 120, that is, to the lead terminals 123 of the flexible printed circuit board 120, by soldering, etc., while the temperature/humidity sensor module 110 is inserted into the through hole 131. Bonding between the connection terminals 134 and the lead terminals 123 may be weak if only soldering is made therebetween. In order to strengthen the bonding between the connection terminals 134 and the lead terminals 123, by forming a plurality of holes in a portion of the flexible printed circuit board 120 where the substrate assembly 130 contacts, filling the holes with epoxy, and hardening the epoxy, the flexible printed circuit board 120 is more tightly coupled with the substrate assembly 130.

Since the temperature/humidity sensor module 110 is inserted into the through hole 131 of the substrate assembly 130, and coupled with the substrate assembly 130 through the flexible printed circuit board 120, the fog sensing apparatus 100 can be easily attached on the glass surface 10 of the vehicle window, while having a compact structure.

Also, the substrate assembly 130 includes substrate terminals 135 which are connected to connector terminals 144 (which will be described later) of the case 140 by soldering, etc.

Meanwhile, in order to obtain an exact dew point temperature, an inside temperature sensor 132 for measuring the inside temperature of a vehicle can be provided. Also, the substrate assembly 130 further includes a control circuit module 133.

The control circuit module 133 compares a dew point temperature obtained from values measured by the humidity sensor and the inside temperature sensor 132, with a glass surface temperature measured by the glass surface temperature sensor of the temperature/humidity sensor module 110, and outputs a fog detection signal according to the result of the comparison.

That is, the control circuit module 133 obtains the dew point temperature according to a well-known equation for calculating a dew point temperature from a relative humidity value and an inside temperature value. Then, the control circuit module 133 compares the dew point temperature with the glass surface temperature, determines that fog is formed on the glass surface 10 of the vehicle window if the dew point temperature is higher than the glass surface temperature, and outputs a fog detection signal. The fog detection signal is provided to the air conditioning system of the vehicle to prevent fog from forming on the glass surface 10 of the vehicle window.

The case 140 covers the substrate assembly 130 to protect the substrate assembly 130 when the flexible printed circuit board 120 and the substrate assembly 130 are attached to the glass surface 10 of the vehicle window, which will be described later. The case 140 has a concave portion 141 into which the substrate assembly 130 is inserted. The case 140 is mechanically coupled with and fixed on the substrate assembly 130, or is attached to and fixed on the substrate assembly 130 by an adhesive layer, etc.

An air inflow channel 142 is formed at a location of the case 140 which corresponds to the temperature/humidity sensor module 110. The air inflow channel 142 enables air to flow into the temperature/humidity sensor module 110 and into the humidity sensor of the temperature/humidity sensor module 11 along the glass surface 10 of the vehicle window. A plurality of air inflow channels 142 may be formed in a lattice form in the corresponding location of the case 140.

A connector 143 for supplying power to the control circuit module 133 and receiving/outputting data from/to the control circuit module 133 is provided in a side of the case 140. The connector 143 is connected to the control circuit module 133 through connector terminals. The substrate assembly 130 includes substrate terminals 135 which are drawn out from the control circuit module 133 and connected to the connector terminals 144 by soldering, etc. Meanwhile, in the case 140, a hole is formed toward the connector terminals 144 to facilitate soldering of the connector terminals 144 and the substrate terminals 135, and the hole is covered by a cover member 146 or with a molding material after soldering.

The connector 143 can be connected to a control box for controlling electrical apparatus components of a vehicle, through a wire harness. Therefore, if the control box receives a fog detection signal from the control circuit module 133 through the connector 143, the control box performs dehumidification using the air conditioning system to prevent fog from forming on the glass surface 10 of the vehicle window.

Figure 4:
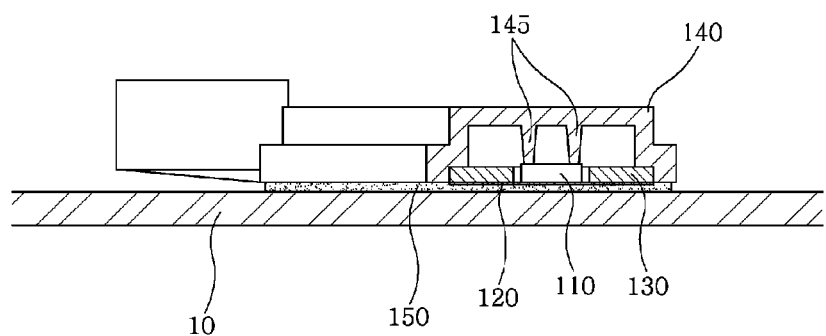
FIG. 4 is a cross-sectional view of the fog sensing apparatus illustrated in FIG. 1 which is attached to a glass surface of a vehicle window.

In the case 143, pressure projections 145 are formed in a location corresponding to the temperature/humidity sensor module 110. The pressure projections 145 are protruded toward the temperature/humidity sensor module 110. As illustrated in FIG. 4, the pressure projections 145 apply pressure to the temperature/humidity sensor module 110 toward the vehicle window when the fog sensing apparatus 100 is attached to the vehicle window via the adhesive layer 150, thereby causing the flexible printed circuit board 120 to be adhered closely to the adhesive layer 150 and simultaneously causing the adhesive layer 150 to be adhered closely to the vehicle window. Therefore, a temperature of the glass surface 10 of the vehicle window can be more accurately measured.

The fog sensing apparatus 100 is attached to and fixed on the vehicle window by the adhesive layer 150. The adhesive layer 150 may extend over the whole area of the substrate assembly 130 so that the adhesive layer 150 can be adhered closely to the glass surface 10 of the vehicle window. Also, it is preferable that the adhesive layer 150 has thermal conductivity as well as adhesive property in order to facilitate heat transfer from the glass surface 10 of the vehicle window to the glass surface temperature sensor of the temperature/humidity sensor module 110. Also, it is preferable that the adhesive layer 150 is made of a soft material so that the adhesive layer 150 has sufficient adhesive property when the adhesive layer 150 is adhered to a curved glass surface.

INDUSTRIAL APPLICABILITY

The present invention can be applied to an apparatus for preventing fog from forming on the glass surface of a vehicle window.

The invention claimed is:

1. A fog sensing apparatus for a vehicle window, comprising:
   an adhesive layer having a top adhesive surface and a bottom adhesive surface, the bottom adhesive surface being capable of adhering to a glass surface of the vehicle window;
   a flexible printed circuit board attached directly on the top adhesive surface of the adhesive layer, the flexible printed circuit having a conductive pattern;
   a temperature and humidity sensor module mounted directly on the conductive pattern of the flexible printed circuit board, the temperature and humidity sensor module including a glass surface temperature sensor for measuring a temperature of the glass surface of the vehicle window, and a humidity sensor for measuring relative humidity around the glass surface of the vehicle window;
   a substrate assembly having a through hole for the temperature and humidity sensor module to pass through, and connection terminals connected to the conductive pattern; and
   a case covering the substrate assembly, the substrate assembly interposed between the case and the flexible printed circuit board,
   wherein the adhesive layer has heat conductivity to facilitate heat transfer from the glass surface of the vehicle window to the glass surface temperature sensor of the temperature and humidity sensor module.

2. The fog sensing apparatus of claim 1, wherein the substrate assembly further comprises an inside temperature sensor for measuring an inside temperature of the vehicle.

3. The fog sensing apparatus of claim 2, wherein the substrate assembly further comprises a control circuit module comparing a dew point temperature obtained from a value measured by the humidity sensor and a value measured by the inside temperature sensor, with a glass surface temperature measured by the glass surface temperature sensor, and outputting a fog detection signal according to the result of the comparison.

4. The fog sensing apparatus of claim 3, wherein the case further comprises a connector coupled with the control circuit module to supply power to the control circuit module and receive data from the control circuit module or output data to the control circuit module.

5. The fog sensing apparatus of claim 1, wherein the flexible printed circuit board has a thickness less than 0.1 mm.

6. The fog sensing apparatus of claim 1, wherein the case further comprises a pressure projection formed at a location corresponding to the temperature and humidity sensor module to apply pressure to the temperature/humidity sensor module toward the glass surface of the vehicle window.

7. The fog sensing apparatus of claim 1, wherein a filter for removing foreign materials from air supplied through an air inflow hole of the case is installed in an air inflow channel of the humidity sensor of the temperature and humidity sensor module.

8. The fog sensing apparatus of claim 1, wherein the temperature and humidity sensor module is of a Micro Electro Mechanical Systems (MEMS) type.

* * * * *